(12) United States Patent
Zimmerling

(10) Patent No.: US 11,938,319 B2
(45) Date of Patent: Mar. 26, 2024

(54) CYLINDRICAL IMPLANT MAGNET OPTIMIZED FOR MRI

(71) Applicant: MED-EL Elektromedizinische Geraete GmbH, Innsbruck (AT)

(72) Inventor: Martin Zimmerling, Patsch (AT)

(73) Assignee: MED-EL ELEKTROMEDIZINISCHE GERAETE GMBH, Innsbruck (AT)

( * ) Notice: Subject to any disclaimer, the term of this patent is extended or adjusted under 35 U.S.C. 154(b) by 254 days.

(21) Appl. No.: 17/281,888

(22) PCT Filed: Oct. 28, 2019

(86) PCT No.: PCT/US2019/058249
§ 371 (c)(1),
(2) Date: Mar. 31, 2021

(87) PCT Pub. No.: WO2020/092185
PCT Pub. Date: May 7, 2020

(65) Prior Publication Data
US 2021/0386999 A1  Dec. 16, 2021

Related U.S. Application Data

(60) Provisional application No. 62/751,756, filed on Oct. 29, 2018.

(51) Int. Cl.
*A61N 1/36* (2006.01)
*A61N 1/08* (2006.01)
(Continued)

(52) U.S. Cl.
CPC ......... *A61N 1/36038* (2017.08); *A61N 1/086* (2017.08); *A61N 1/375* (2013.01); *H04R 25/606* (2013.01); *H04R 2225/67* (2013.01)

(58) Field of Classification Search
CPC .... A61N 1/36038; A61N 1/086; A61N 1/375; H04R 25/606; H04R 2225/67
See application file for complete search history.

(56) References Cited

U.S. PATENT DOCUMENTS 5,824,022 A * 10/1998 Zilberman ......... A61N 1/36038
607/57
9,872,115 B2  1/2018 Kennes
(Continued)

OTHER PUBLICATIONS

International Searching Authority/US, International Search Report and Written Opinion of the International Seraching Authority, Application No. PCT/US2019/058249, dated Dec. 31, 2019, 15 pages.

*Primary Examiner* — Catherine M Voorhees
(74) *Attorney, Agent, or Firm* — BURNS & LEVINSON LLP

(57) ABSTRACT

A magnet arrangement for a hearing implant device is described. A magnet case is contained within an implantable device and has a central case axis of symmetry that is perpendicular to the outermost surface of the implantable device. The magnet case is configured to be freely rotatable within the implantable device about the case axis of symmetry. An implant magnet is contained within the magnet case and consists of a single cylindrical magnet having a central magnet axis of symmetry perpendicular to the case axis of symmetry. The implant magnet is configured to be freely rotatable within the magnet case about the magnet axis of symmetry.

19 Claims, 7 Drawing Sheets

(51) Int. Cl.
*A61N 1/375* (2006.01)
*H04R 25/00* (2006.01)

(56) References Cited

U.S. PATENT DOCUMENTS

| | | | |
|---|---|---|---|
| RE48,647 E * | 7/2021 | Zimmerling | H04L 12/189 |
| 11,638,823 B2 * | 5/2023 | Brehm | A61N 1/37211 |
| | | | 607/137 |
| 2002/0097890 A1 | 7/2002 | Kobayashi et al. | |
| 2011/0264172 A1 * | 10/2011 | Zimmerling | A61N 1/36036 |
| | | | 607/60 |
| 2016/0037273 A1 | 2/2016 | Gustafsson | |
| 2018/0296826 A1 * | 10/2018 | Lee | H01F 7/0205 |
| 2020/0197702 A1 * | 6/2020 | Eigentler | A61N 1/36038 |

* cited by examiner

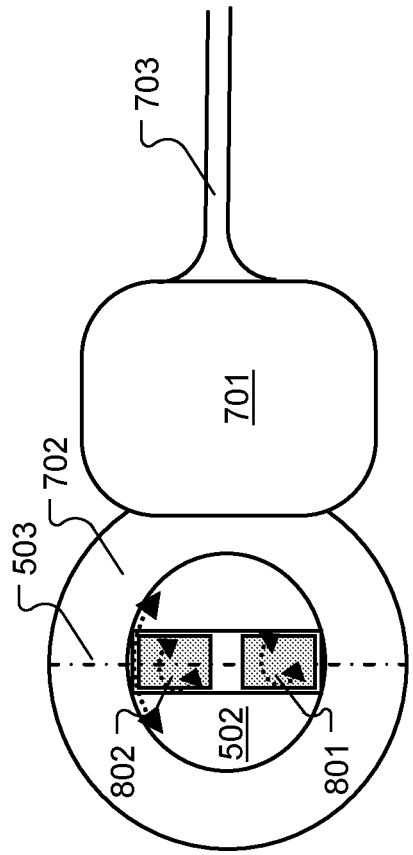
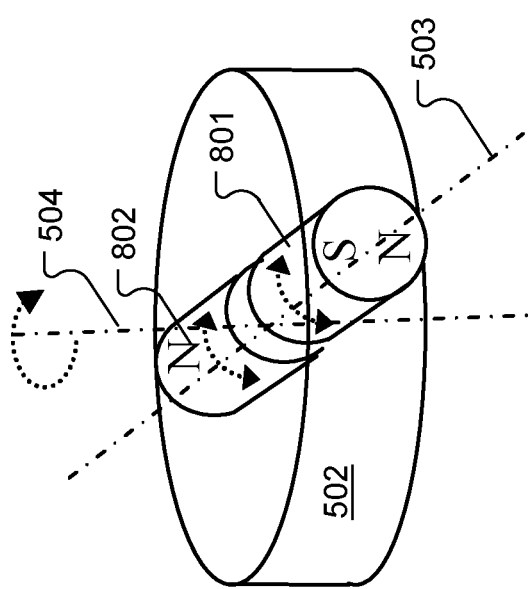
Fig. 8B
Fig. 8A

CYLINDRICAL IMPLANT MAGNET OPTIMIZED FOR MRI

This application is the national phase entry of International Patent Application No. PCT/US2019/058249 filed Oct. 28, 2019, which claims priority from U.S. Provisional Patent Application 62/751,756, filed Oct. 29, 2018, the disclosures of which are incorporated herein by reference in their entirety.

This application claims priority from U.S. Provisional Patent Application 62/751,756, filed Oct. 29, 2018, which is incorporated herein by reference in its entirety.

FIELD OF THE INVENTION

The present invention relates to implantable hearing devices such as cochlear implants, and specifically, to implantable magnets in such devices.

BACKGROUND ART

Some hearing implants such as Middle Ear Implants (MEI's) and Cochlear Implants (CI's) employ cooperating attachment magnets located in the implant and the external part to magnetically hold the external part in place over the implant. For example, as shown in FIG. 1, a typical cochlear implant system may include an external transmitter device 101 containing transmitting coils 102 and an external attachment magnet 103. The external attachment magnet 103 has a conventional cylindrical disc-shape and a north-south magnetic dipole having an axis that is perpendicular to the skin of the patient to produce external magnetic field lines 104 as shown. Implanted under the patient's skin is a corresponding receiver assembly 105 having similar receiving coils 106 and an implant magnet 107. The implant magnet 107 also has a cylindrical disc-shape and a north-south magnetic dipole having a magnetic axis that is perpendicular to the skin of the patient to produce internal magnetic field lines 108 as shown. The internal receiver device 105 is surgically implanted and fixed in place within the patient's body. The external transmitter device 101 is placed in proper position over the skin covering the internal receiver assembly 105 and held in place by interaction between the internal magnetic field lines 108 and the external magnetic field lines 104. Rf signals from the transmitter coils 102 couple data and/or power to the receiving coil 106 which is in communication with an implanted processor module (not shown).

One problem arises when the patient undergoes Magnetic Resonance Imaging (MRI) examination. Interactions occur between the implant magnet and the applied external magnetic field for the MRI. As shown in FIG. 2, the direction magnetization $\bar{m}$ of the implant magnet 202 is essentially perpendicular to the skin of the patient. In this example, the strong static magnetic field $\bar{B}$ from the MRI creates a torque $\bar{T}$ on the internal magnet 202, which may displace the internal magnet 202 or the whole implant device 201 out of proper position. Among other things, this may damage the adjacent tissue in the patient. In addition, the external magnetic field $\bar{B}$ from the MRI may reduce or remove the magnetization $\bar{m}$ of the implant magnet 202 so that it may no longer be strong enough to hold the external transmitter device in proper position. The implant magnet 202 may also cause imaging artifacts in the MRI image, there may be induced voltages in the receiving coil, and hearing artifacts due to the interaction of the external magnetic field $\bar{B}$ of the MRI with the implanted device. Torque and forces acting on the implant magnet and demagnetization of the implant magnet are especially an issue with MRI field strengths exceeding 1.5 Tesla.

Thus, for many existing implant systems with magnet arrangements, it is common to either not permit MRI, or at most limit use of MRI to lower field strengths. Other existing solutions include use of a surgically removable magnets, spherical implant magnets (e.g. U.S. Pat. No. 7,566,296), and various ring magnet designs (e.g., U.S. Provisional Patent 61/227,632, filed Jul. 22, 2009).

U.S. Pat. No. 8,634,909 describes an implant magnet having a magnetic dipole with a magnetic axis that is parallel to the end surfaces of a disc shaped implant magnet—that is, perpendicular to the conventional magnetic axis of a disc-shaped implant magnet. The magnet is then held in a magnet receptacle that allows the magnet to rotate about its center axis in response to an external magnetic field such as from an MRI to realign and avoid creating torque. But this rotation is only possible around a single axis.

FIG. 3 shows the head of a patient with bilateral cochlear implants 301 having such an implant magnet in the presence of a typical MRI scanning magnetic field $B_0$, which is aligned along the central symmetry axis of the patient. The magnetization plane of the cochlear implants 301 is angled with respect to the magnetic field $B_0$ at some relative angle $\alpha_{B0}$ as shown in FIG. 3, which can create an undesirable residual torque on the cochlear implants 301.

FIG. 4 shows in greater detail the geometry of an implant magnet 401 with a magnetic dipole m that is parallel to the skin, and an MRI scanning magnetic field $B_0$ aligned along the central symmetry axis. The cylindrical disc shape of the implant magnet 401 also has a height h and a diameter Ød. Depending on the specific position of the implant, there will be a relative angle $\alpha_{B0}$ between the direction of the magnetic dipole m of the implant magnet 401 and the static magnetic field $B_0$. This relative angle $\alpha_{B0}$ leads to a torque force on the implant magnet 401, where the torque T=m×$B_0$, and the correlated force is F=T/D, where D is the distance or diameter of the stiff structure surrounding the implant magnet 401.

The actual such implant magnet that is used in the Med-El Synchrony implant is specified for a relative angle $\alpha_{B0}$ of the head of up to ±30°. This value is sufficient in clinical practise. When taking variations in anatomy of the skull and implant position relative to the head into consideration, the relative angle $\alpha_{B0}$ between the implant magnet and the static magnetic field $B_0$ is even higher. The upper limit for the relative angle $\alpha_{B0}$ is needed to limit the mechanical torque acting on the implant magnet and to avoid magnet weakening with very high $B_0$ values.

The disc-shaped magnet could be replaced by a spherical magnet, in which case there would be no residual torque during MRI regardless of the head orientation. But the diameter of such a spherical implant magnet needed to achieve sufficient magnetic attraction force between the implant magnet and the external magnet would be quite large, which is another different problem. A spherical implant magnet also would project out of the coil plane, and so additional surgical steps would be required such as milling a recess into the skull for accommodating the magnet.

It also has been suggested to use a set of multiple cylindrical magnets which are magnetized perpendicular to the cylindrical axis and embedded into a magnet frame and case which can turn around the central axis of the case (see e.g., WO2017/105510, which is incorporated herein by reference in its entirety). However, since there are always two or more implant magnets involved, those magnets influence each other, and so they try to maintain an orientation where two neighboring magnets always have their poles facing to poles of opposite polarity of the other magnets. These magnets form a magnetic dipole as described above and shown in FIG. 4. When the patient turns his head out of the straight head orientation (i.e. with increasing angle $\alpha_{B0}$ between the implant magnet and the main magnetic field $B_0$), a torque needs to be applied until the magnets no longer keep their magnetic orientation where neighbouring magnets have their poles facing to poles of opposite polarity of the other magnets but all of a sudden align their magnetic dipole according to the static magnetic field $B_0$. Then the torque is zero. When turning the head back in the original orientation, as soon the angle $\alpha_{B0}$ between the implant magnet and the main magnetic field $B_0$ falls below a certain angle, a torque is present again. With further reduction of $\alpha_{B0}$ the torque reduces again until it disappears.

SUMMARY OF THE INVENTION

Embodiments of the present invention are directed to a magnet arrangement for a hearing implant device. An implantable device contains signal processing circuitry configured for receiving an implant communications signal transmitted by an external transmitting coil through overlying skin of an implanted patient. The implantable device includes an outermost surface that is adapted to lie between the overlying skin and underlying skull bone of the implanted patient. A magnet case is contained within the implantable device and has a central case axis of symmetry that is perpendicular to the outermost surface. The magnet case is configured to be freely rotatable within the implantable device about the case axis of symmetry. An implant magnet is contained within the magnet case and is configured to cooperate with a corresponding external holding magnet in an external device located over the overlying skin to magnetically hold the external device against the overlying skin. The implant magnet consists of a single cylindrical magnet that has a central magnet axis of symmetry perpendicular to the case axis of symmetry, and the implant magnet is configured to be freely rotatable within the magnet case about the magnet axis of symmetry.

In further specific embodiments, there also may be a pair of gravity masses configured to lie on opposing sides of the implant magnet offset from the case axis of symmetry so as to shift a center of gravity of the magnet case and its contents away from the case axis of symmetry. There also may be a magnet case coating that covers an outer surface of the magnet case and/or a magnet holder that surrounds an outer cylindrical surface of the implant magnet.

The single cylindrical magnet may be characterized by a cylinder diameter and a cylinder circumference, wherein the single cylindrical magnet has a magnetization direction across the cylinder diameter with magnetic poles located opposite each other on the cylinder circumference. Or the single cylindrical magnet may be characterized by opposing cylinder ends and a center cylinder axis, wherein the single cylindrical magnet has a magnetization direction along the center cylinder axis with magnetic poles located opposite each other at each cylinder end.

The magnet case may have a cylindrical shape or a conical section shape. The magnet case may be formed of metallic material or a biocompatible non-metallic material.

Embodiments of the present invention also include a hearing implant system containing a magnet arrangement according to any of the foregoing.

BRIEF DESCRIPTION OF THE DRAWINGS

FIGS. 8A-8B show another alternative embodiment of the present invention.

DETAILED DESCRIPTION OF SPECIFIC EMBODIMENTS

Embodiments of the present invention are directed to an improved implant magnet arrangement that is limited to a single cylindrical implant magnet with a central magnet axis of symmetry that is perpendicular to the axis of symmetry of a cylindrical magnet case in which the implant magnet is held. In addition, the implant magnet can freely rotate within the magnet case about the magnet axis of symmetry and the magnet case also is free to rotate about its case axis of symmetry. This magnet arrangement is torque-free regardless of the orientation of the implant (and thus the head).

Figure 1:
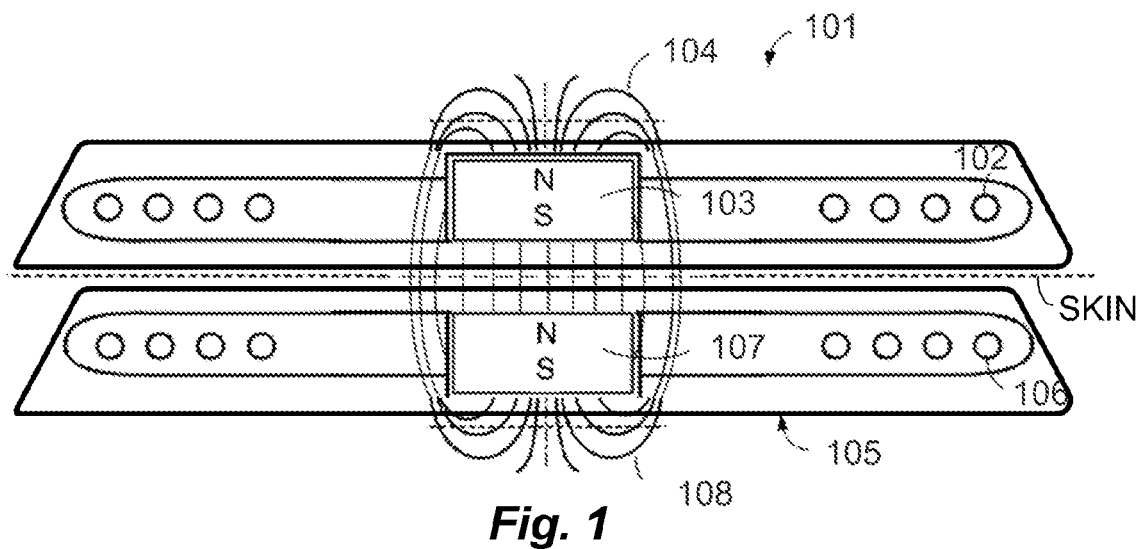
FIG. 1 shows portions of a typical cochlear implant system and the magnetic interaction between the implant magnet and the external holding magnet.
Figure 2:
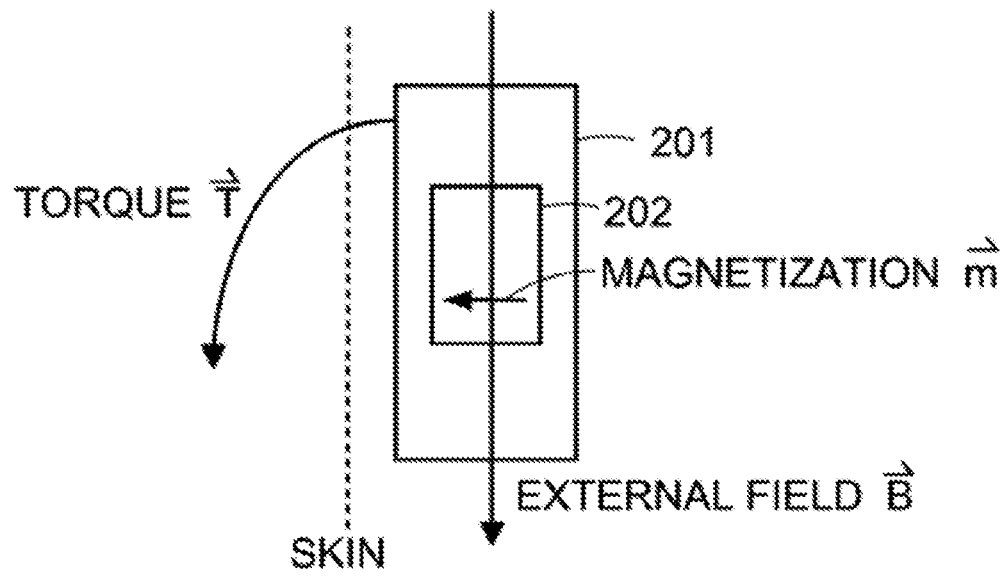
FIG. 2 illustrates the force interactions that can occur between an implant magnet and the applied external magnetic field for an MRI system.
Figure 3:
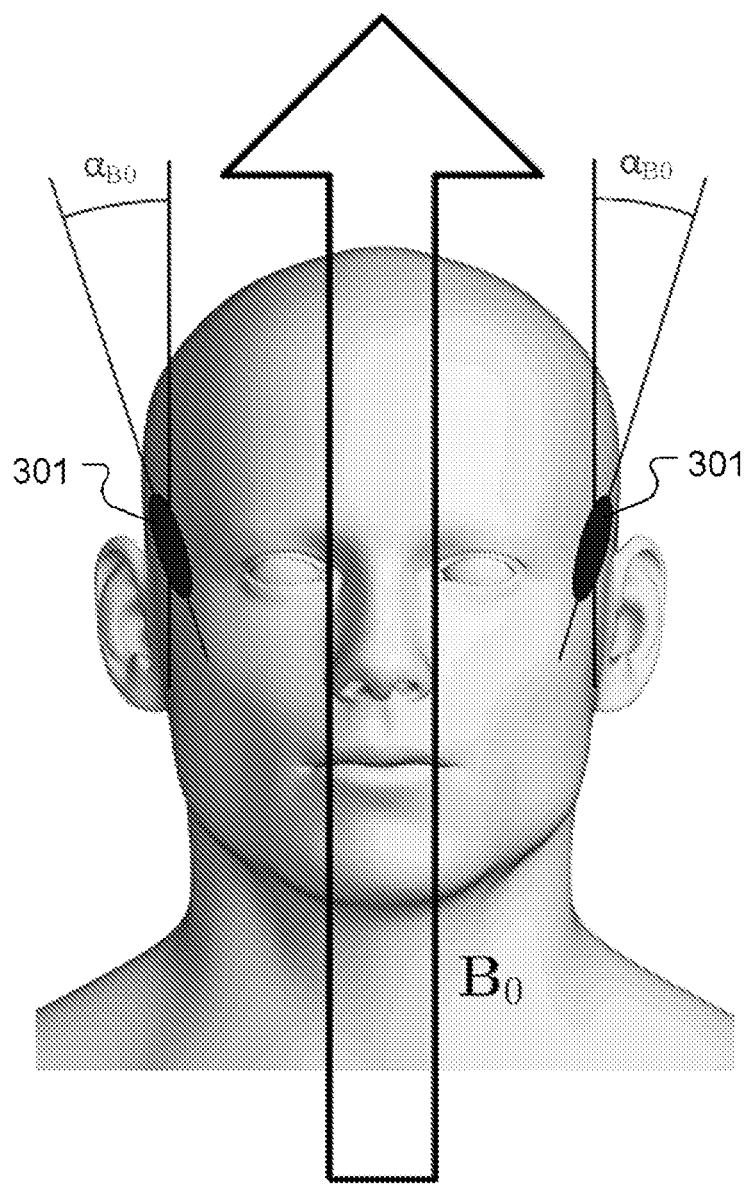
FIG. 3 the head of a patient with bilateral cochlear implants in the presence of a typical MRI scanning magnetic field.
Figure 4:
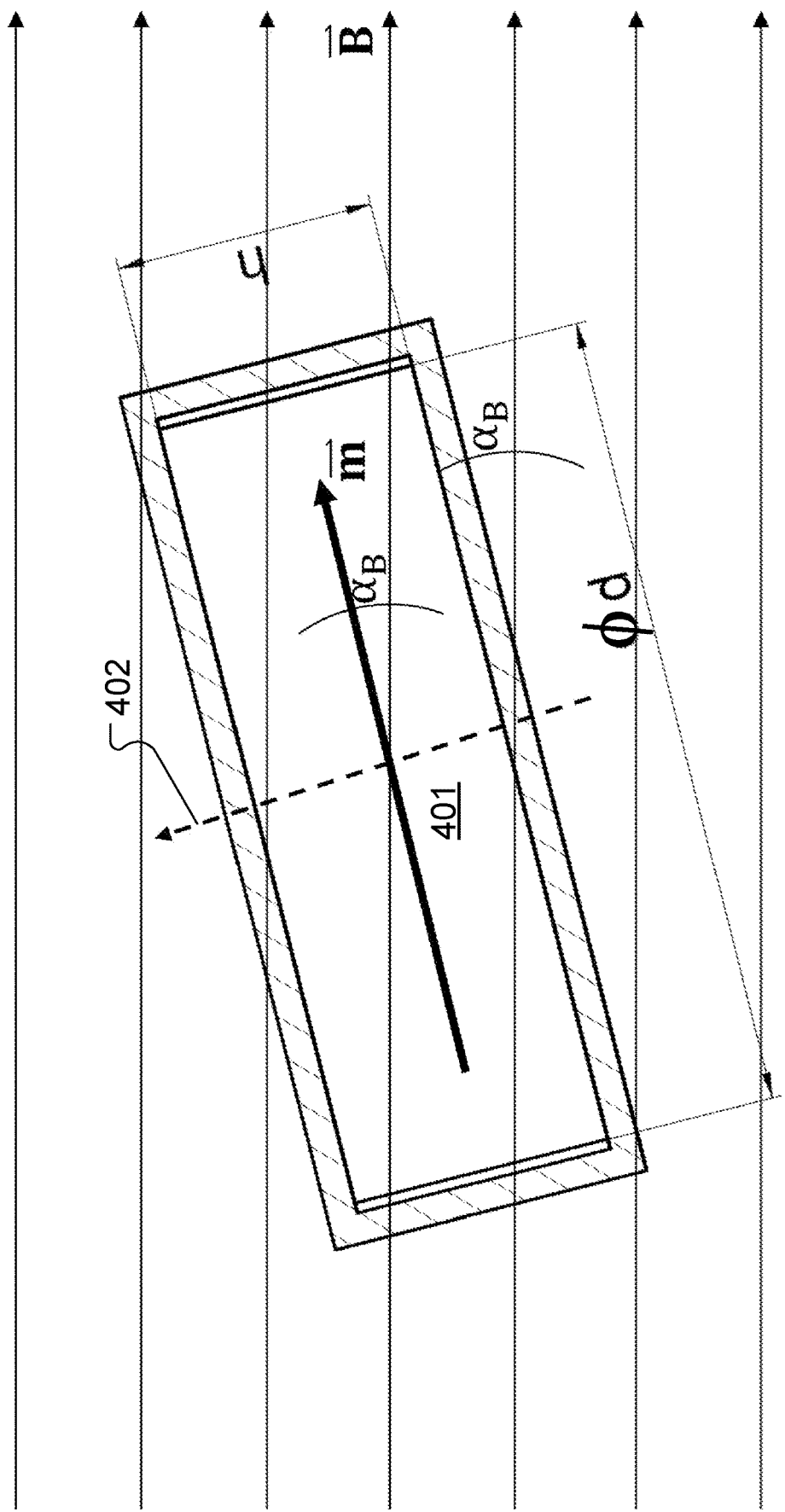
FIG. 4 shows geometry of an implant magnet with a magnetic dipole parallel to the skin and an MRI scanning magnetic field.
Figure 5B:
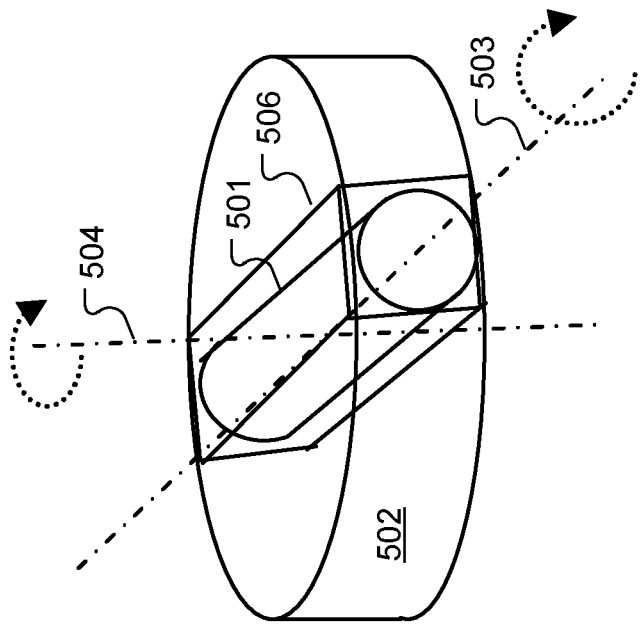
FIGS. 5A-5B show a magnet and magnet case according to an embodiment of the invention.
Figure 5A:
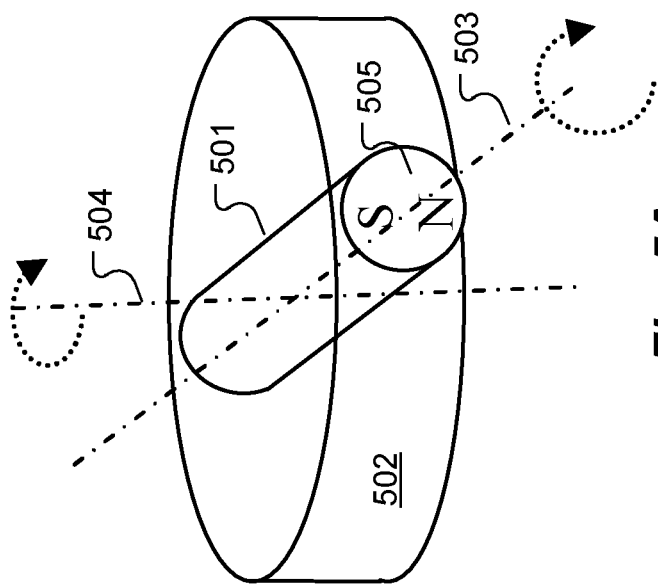

FIGS. 5A-5B show an implant magnet and magnet case according to an embodiment of the invention. A magnet case 502 has a central case axis of symmetry 504 that is perpendicular to the outermost surface of an implantable device (see FIGS. 7A-7B—typically the magnet case 502 is surrounded by the receiver coil of the implant device as discussed below). The magnet case 502 is configured to be freely rotatable within the implantable device about the case axis of symmetry 504. The magnet case 502 may be metallic (e.g. made of titanium), or it may be made of a biocompatible non-metallic material (e.g. PEEK, FEP, PTFE, PSU, etc.) and may be coated (e.g. with Parylene). The magnet case 502 may be adapted to facilitate long-term hermetic encapsulation, and/or it may be adapted to be surgically removable for minimized susceptibility to MRI artifacts.

A single cylindrical implant magnet 501 is contained within the magnet case 502 and has its own central magnet axis of symmetry 503 that is perpendicular to the case axis of symmetry 504. The implant magnet 501 is configured to be freely rotatable within the magnet case 502 about the magnet axis of symmetry 503. FIG. 5B shows a variant in which the implant magnet 501 is contained within its own separate magnet holder device 506 that is in turn contained within the magnet case 502. The magnet holder device 506, like the magnet case 502, also may be metallic (e.g. made of titanium), or it may be made of a biocompatible non-metallic material (e.g. PEEK, FEP, PTFE, PSU, etc.) and may be coated (e.g. with Parylene). Like with FIG. 5A, the magnet case 502 is configured to be freely rotatable within the implanted device around axis 504, or in a variant, the magnet holder device 506 may be freely rotatable within the magnet case 502.

Although the foregoing is described with regards to a cylindrical implant magnet 501 and a cylindrical magnet case 502, in other specific embodiments, other specific shapes may be used. For example, in some embodiments, the magnet case 502 may have a prismatic (i.e. box-shaped) geometry or a conical or double-conical shape. When the magnet case 502 represents a box-shaped, relatively tight encapsulation, it may be made of metal (e.g. titanium) for optimal long-term hermetic encapsulation, and when the magnet case 502 is non-metallic, this keeps the geometric area of metal in the implant coil part small, and thus keeps losses in the inductive link (signal and energy) low.

In specific embodiments, the magnetization direction of the implant magnet 501 may be "diametrically magnetized" across the diameter 505 of the holding magnet 501 so that the magnetic poles are located at opposing locations on the circumference of the diameter 505. For example, this is the magnetization direction used in the Med-El Synchrony magnet. Alternatively, the magnetization direction of the implant magnet 502 may be in the older more conventional "axially magnetized" direction along the central magnet axis of symmetry 503 with one magnetic pole at one end of the cylinder shape and the other magnetic pole at the opposite end of the cylinder shape.

Figure 6B:
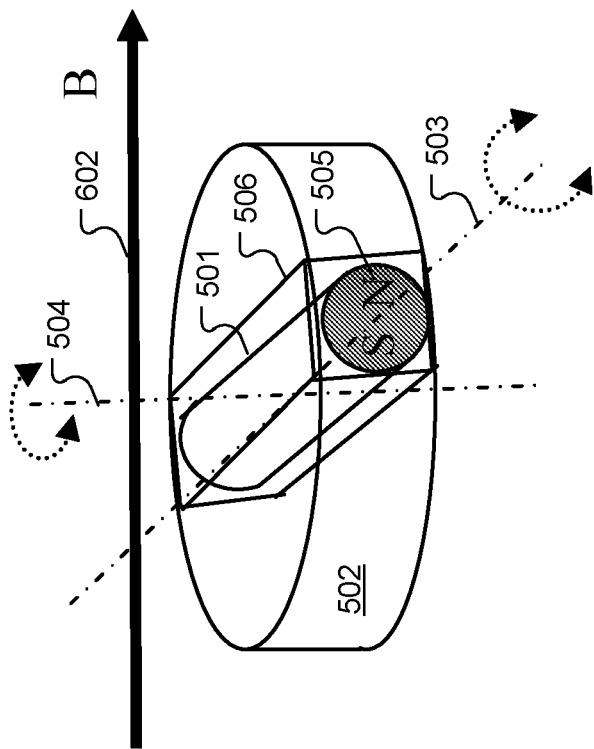
FIGS. 6A-6B show a magnet and magnet case according to FIGS. 5A-5B in the presence of an external device magnet and an MRI magnetic field respectively.
Figure 6A:
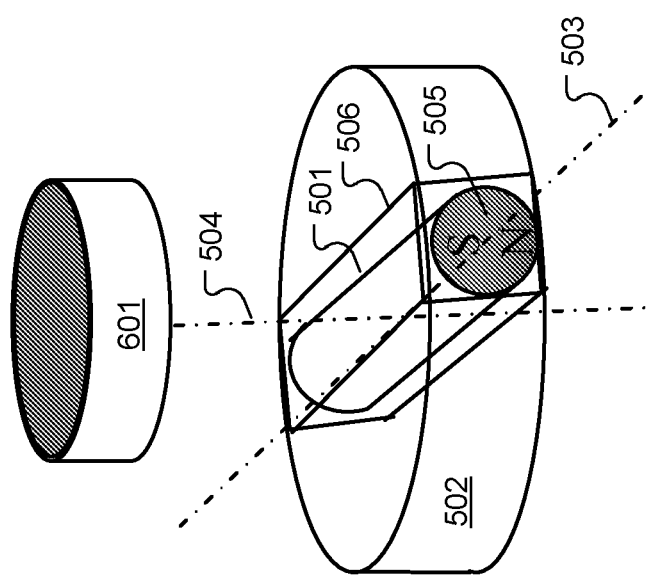

FIGS. 6A-6B show an implant magnet 501 and magnet case 502 according to FIGS. 5A-5B in the presence of an external device holding magnet 601 and an MRI magnetic field 602 respectively. In the specific case of FIG. 6A, when an external holding magnet 601 is placed on the overlying skin of the patient over the implant magnet 501, the diametrically magnetized cylindrical implant magnet 501 will be oriented with a vertical magnetization (magnetization direction parallel to the case axis of symmetry 504). The implant magnet 501 cooperates with the external device holding magnet 601 to magnetically hold the external device against the overlying skin over the implant magnet 501. The magnetization direction of the corresponding external holding magnet 601 preferably though not necessarily matches the magnetization direction of the implant magnet 501.

With an external MRI magnetic field 602 that is perpendicular to the case axis of symmetry 504 as shown in FIG. 6B (e.g. the static magnetic field in an MRI environment), the implant magnet 501 within the magnet case 502 rotates about the case axis of symmetry 504 and about the magnet axis of symmetry 503 such that the magnet axis of symmetry 503 is perpendicular to the external magnetic field 602. This aligns magnetization direction of the implant magnet 501 to be parallel that of the external magnetic field 602 (behaving just like a spherical magnet). Therefore, regardless of the orientation of the head (and thus the implant), the implant magnet 501 is safe against demagnetization and free of torque even at very high MRI field strengths (e.g., 3 T).

Figure 7A:
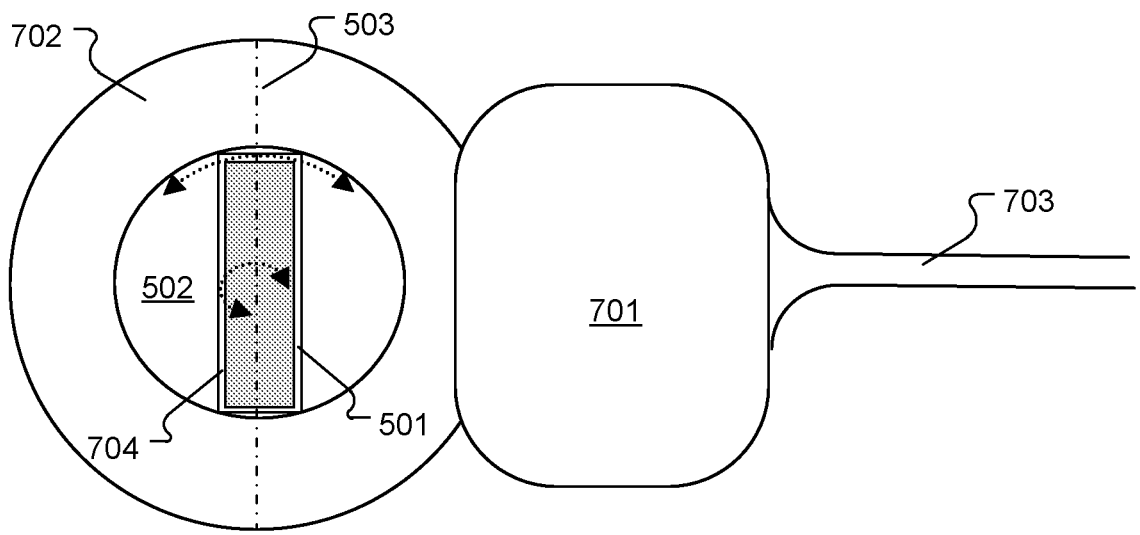
FIGS. 7A-7B show details of various alternative embodiments of the present invention.
Figure 7B:
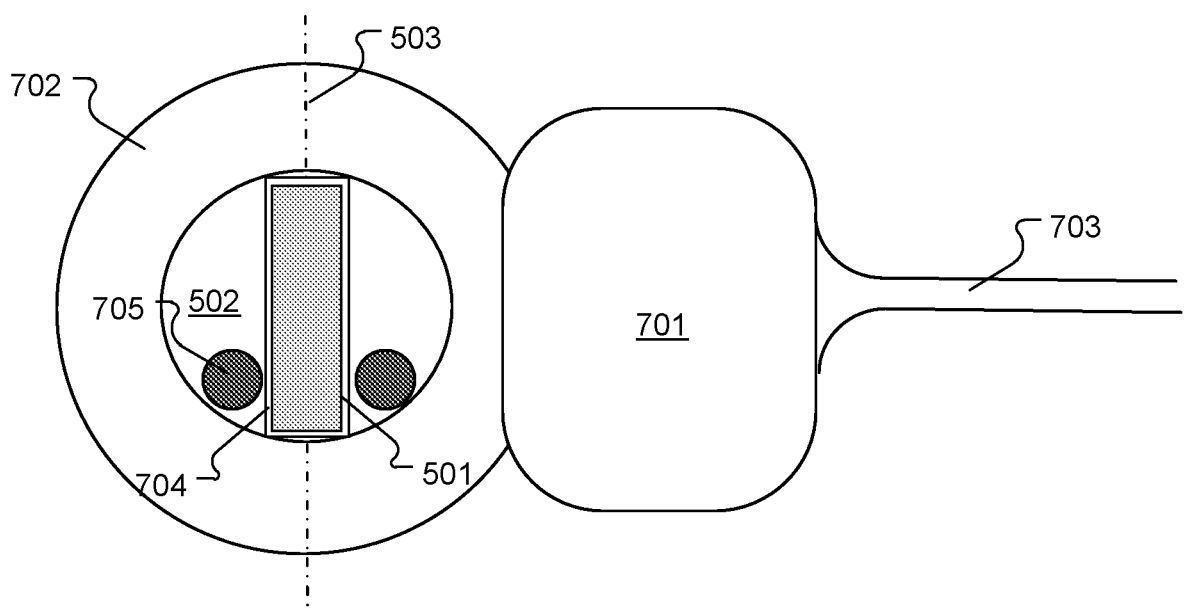

FIGS. 7A-7B show details of various alternative embodiments of the present invention, also showing how the implant magnet 501 and the magnet case 502 are located to be surrounded by an implant receiving coil 702 that is connected to an implantable device 701 that contains signal processing circuitry configured for receiving an implant communications signal transmitted by an external transmitting coil through overlying skin of an implanted patient. The implantable device 701 includes an outermost surface that is adapted to lie between the overlying skin and underlying skull bone of the implanted patient and generates the electrical stimulation signals that are delivered by an implant lead 703. The outer surface of the implant magnet 501 that is shown in FIG. 7A has a long term corrosion-resistant coating 704, and the magnet case 502 also may have such a coating.

FIG. 7B shows a specific embodiment with a pair of gravity masses 705 that configured to lie on opposing sides of the implant magnet 501 offset from the case axis of symmetry 504 so as to shift a center of gravity of the magnet case 502 and its contents away from the case axis of symmetry 504. This keeps the magnet axis of symmetry 503 of the cylindrical implant magnet 501 vertical regardless of head orientation and the position of the implantable device 701 within the head when there is no magnetic field component in the plane of the receiving coil 702. This allows a higher magnet shear force in vertical orientation between the implant magnet 501 and the external device holding magnet 601. This is advantageous since in vertical acceleration and forces acting on external components (e.g., patient coils and single-unit processors) are dominant over horizontal acceleration or forces.

FIGS. 8A-8B show another alternative embodiment of the present invention with two diametrically magnetized cylindrical magnets 801 and 802, each with the same magnet axis of symmetry 503 around which each can individually rotate. When the external device holding magnet 601 is diametrically magnetized, then with one of the two cylindrical implant magnets 801 or 802, the North magnetic pole would face towards the overlying skin, and with the other cylindrical magnet 802 or 801, the South magnetic pole would face towards the overlying skin. This would improve the magnetic fixation with an external diametrically magnetized external device holding magnet 601. The two implant magnets 801 and 802 may be hermetically encapsulated individually or together.

Although various exemplary embodiments of the invention have been disclosed, it should be apparent to those skilled in the art that various changes and modifications can be made which will achieve some of the advantages of the invention without departing from the true scope of the invention.

What is claimed is:

1. A hearing implant device comprising:
   signal processing circuitry configured for receiving an implant communications signal transmitted by an external transmitting coil through overlying skin of a patient, wherein the hearing implant device includes an outermost surface adapted to lie between the overlying skin and underlying skull bone of the patient;
   a magnet case contained within the hearing implant device and having a central case axis of symmetry perpendicular to the outermost surface, wherein the magnet case is configured to be rotatable within the hearing implant device about the central case axis of symmetry;
   an implant magnet contained within the magnet case and configured to cooperate with an external holding magnet in an external device located over the overlying skin to magnetically hold the external device against the overlying skin, wherein the implant magnet consists of a single cylindrical magnet having a magnet axis of symmetry perpendicular to the central case axis of symmetry, and wherein the implant magnet is configured to be rotatable within the magnet case about the magnet axis of symmetry; and a pair of gravity masses configured to lie on opposing sides of the implant magnet equally offset from the magnet axis of symmetry and offset from the central case axis of symmetry to shift a center of gravity of the magnet case and the implant magnet away from the central case axis of symmetry, the pair of gravity masses further configured to keep the magnet axis of symmetry in a vertical orientation aligned with a gravitational direction when no external magnetic field is applied in a plane of the magnet case.

2. The hearing implant device according to claim 1, further comprising:

a magnet case coating covering an outer surface of the magnet case.

3. The hearing implant device according to claim 1, further comprising:

a magnet holder surrounding an outer cylindrical surface of the implant magnet.

4. The hearing implant device according to claim 1, wherein the single cylindrical magnet includes a cylinder diameter and a cylinder circumference, and wherein the single cylindrical magnet has a magnetization direction across the cylinder diameter with magnetic poles located opposite each other on the cylinder circumference.

5. The hearing implant device according to claim 1, wherein the single cylindrical magnet includes opposing cylinder ends and a center cylinder axis, and wherein the single cylindrical magnet has a magnetization direction along the center cylinder axis with magnetic poles located opposite each other at each cylinder end.

6. The hearing implant device according to claim 1, wherein the magnet case has a cylindrical shape.

7. The hearing implant device according to claim 1, wherein the magnet case has a conical section shape.

8. The hearing implant device according to claim 1, wherein the magnet case is formed of metallic material.

9. The hearing implant device according to claim 1, wherein the magnet case is formed of a biocompatible non-metallic material.

10. A hearing implant system containing the hearing implant device according to claim 1.

11. The hearing implant system according to claim 10, further comprising:

the external device, the external device comprising the external transmitting coil configured to transmit the implant communications signal to the hearing implant device and comprising an innermost surface adapted to lie adjacent to the overlying skin; and the external holding magnet in the external device configured to cooperate with the implant magnet of the hearing implant device to magnetically hold the external device against the overlying skin.

12. The hearing implant system according to claim 10, wherein the hearing implant device is a cochlear implant.

13. The hearing implant system according to claim 10, wherein the implant magnet is diametrically magnetized.

14. The hearing implant system according to claim 10, wherein the hearing implant device further includes a second implant magnet having a second magnet axis of symmetry, wherein the second implant magnet is a cylindrical magnet configured to be rotatable within the magnet case about the second magnet axis of symmetry, wherein the second magnet axis of symmetry is the same as the magnet axis of symmetry.

15. The hearing implant system according to claim 14, wherein the implant magnet is diametrically magnetized and the second implant magnet is diametrically magnetized in an opposite direction than the implant magnet.

16. The hearing implant device according to claim 1, wherein the hearing implant device is a cochlear implant.

17. The hearing implant device according to claim 1, wherein the implant magnet is diametrically magnetized.

18. The hearing implant device according to claim 1, further comprising a second implant magnet having a second magnet axis of symmetry, wherein the second implant magnet is a cylindrical magnet configured to be rotatable within the magnet case about the second magnet axis of symmetry, wherein the second magnet axis of symmetry is the same as the magnet axis of symmetry.

19. The hearing implant device according to claim 18, wherein the implant magnet is diametrically magnetized and the second implant magnet is diametrically magnetized in an opposite direction than the implant magnet.

\* \* \* \* \*